United States Patent [19]
Manwaring et al.

[11] Patent Number: 5,891,158
[45] Date of Patent: Apr. 6, 1999

[54] METHOD AND SYSTEM FOR DIRECTING AN INSTRUMENT TO A TARGET

[76] Inventors: Kim H. Manwaring, 3440 E. Tonto Dr., Ahwatukee, Ariz. 85044; Mark L. Manwaring, SW. 1430 Wadleigh Dr., Pullman, Wash. 99163

[21] Appl. No.: 956,826

[22] Filed: Oct. 23, 1997

[51] Int. Cl.$^6$ .................................................... A61B 19/00
[52] U.S. Cl. .................................. 606/130; 606/1; 606/3; 606/96; 600/102; 128/653.1
[58] Field of Search ................................. 606/130, 1, 33, 606/96; 600/102; 128/653.1

[56] References Cited

U.S. PATENT DOCUMENTS

| | | | |
|---|---|---|---|
| 4,651,732 | 3/1987 | Frederick | 128/303 R |
| 5,330,485 | 7/1994 | Clayman et al. | 606/130 |
| 5,383,454 | 1/1995 | Bucholz | 128/653.1 |
| 5,711,299 | 1/1998 | Manwaring et al. | 128/653.1 |

OTHER PUBLICATIONS

Leibinger F.L. Fischer, Stereotactic Guided Microsurgery Catalog, Apr. 1995, Cover page, pp. 2–5.

*Primary Examiner*—Michael Buiz
*Assistant Examiner*—Lien Nao
*Attorney, Agent, or Firm*—Meschkow & Gresham, P.L.C.; Lowell W. Gresham; Jordan M. Meschkow

[57] ABSTRACT

A method and a surgical guidance system (20) direct an instrument to a target (40) located inside a patient (22). The surgical guidance system (20) includes a fixation frame (28), a first arc member (36), a second arc member (38), and first (78) and second (84) electromagnetic (EM) radiative sources. The first arc member (36) and the second arc member (38) are adjustably coupled to rotate about a common axis (48) and are adjusted in response to a target address and at least three marker addresses so that the target (40) is located at the center point of a virtual sphere defined by the arc members. A first electromagnetic (EM) radiative beam (80) and a second electromagnetic (EM) radiative beam (86) are projected from the system (20) and intersect at a line. The line forms a trajectory (146) along which an instrument can be directed to the target (40).

23 Claims, 5 Drawing Sheets

METHOD AND SYSTEM FOR DIRECTING AN INSTRUMENT TO A TARGET

RELATED INVENTIONS

The present invention is related to the following invention:

(1) Surgical Guidance Method and System For Approaching A Target Within A Body, Ser. No. 08/592,053, filed Jan. 26, 1996 and invented by Kim H. Manwaring and Mark L. Manwaring.

TECHNICAL FIELD OF THE INVENTION

The present invention relates generally to the field of surgery. More specifically, the present invention relates to a system and technique for directing a surgical instrument to a target within a body.

BACKGROUND OF THE INVENTION

A number of frame and frameless stereotactic systems have been developed to assist surgeons during various procedures that require an instrument to travel to a target within a body. Typically, a surgeon analyzes images of the body (e.g., CT scans, MRI scans, or PET scans) to determine the location of the target and to determine a desirable trajectory along which the instrument should travel during the surgical procedure.

Frameless stereotactic systems do not require the body to be mechanically fixed directly to a reference frame or other device during the surgical procedure. In addition, frameless stereotactic systems are generally less invasive and allow a surgeon to move a surgical instrument in any desired direction without being restricted by cumbersome mechanical structures. As such, frameless stereotactic systems often reduce the amount of patient trauma associated with certain surgical procedures while providing the surgeon with an adequate amount of positional freedom during surgery.

Conventionally, stereotactic systems attempt to determine the precise location of the surgical instrument relative to a reference point within a coordinate system. Some frameless stereotactic systems utilize sophisticated optical, RF, magnetic, audio, or other methodologies to generate a three dimensional reference volume around the surgical area. Typically, the surgical instrument carries a system-compatible emitter or sensor, and the position of the instrument is determined relative to a number of reference points to facilitate precise location analysis anywhere within the reference volume.

Many surgical procedures require the surgeon to approach a target along a predetermined trajectory. As such, knowledge of the precise location of the surgical instrument within the entire field of operation may not be useful to the surgeon. In other words, the surgeon may primarily need guidance to the predetermined target rather than knowledge of the exact location of the instrument at all times.

Some conventional stereotaxic systems utilize software programs and realtime position feedback techniques to precisely locate the instrument. The data generated by such systems may be difficult to interpret unless the operator is very familiar with the particular system. Thus, surgeons and medical technicians may require extensive training before they can efficiently operate these systems. The complex software and extensive training increases the expense of such systems and results in reluctance by the surgeons to use such systems. Thus, these systems do not get widespread use.

Frameless stereotactic systems may also employ a number of sensitive electronic components. Due to the precision and sensitivity of the electronic components, complex and time consuming calibration and set-up procedures are needed. These procedures may involve the patient prior to commencement of the surgery. This approach may lengthen the amount of time that the patient is under anesthesia thereby increasing the medical risks to the patient.

Other frameless stereotactic systems that precisely locate and orient the instrument may overly restrict the amount of positional freedom available to the surgeon during free-hand surgery. For example, a surgeon may desire to change the trajectory to a target during surgery. A change in the trajectory may be desired to avoid critical or eloquent areas of the brain to the maximum extent possible to prevent permanent brain damage or excessive bleeding. In such a situation, a surgeon may desire to select new surgical entry point. These stereotactic systems may not be able to provide guidance along a new trajectory without extensive, time consuming recalibration and realignment.

SUMMARY OF THE INVENTION

Accordingly, it is an advantage of the present invention that an improved surgical guidance method and system for directing an instrument to a target within a body are provided.

Another advantage of the present invention is that the system is less complex than conventional systems thereby reducing expenses associated with purchase of the surgical guidance system and subsequent training.

Another advantage of the present invention is that calibration and set-up time involving the anesthetized patient is reduced.

Another advantage of the present invention is that a surgeon can quickly and easily select a new entry point and trajectory to the target.

The above and other advantages of the present invention are carried out in one form by a guidance method for directing an instrument to a target. The method calls for deriving a target address for the target and a marker address for each of a plurality of fixed markers. A guidance device is then aligned in response to the target address and marker addresses. The method further calls for projecting a first electromagnetic (EM) radiative beam from the guidance device to produce a first plane of electromagnetic (EM) radiation and projecting a second electromagnetic (EM) radiative beam from the guidance device to produce a second plane of electromagnetic (EM) radiation. The second plane of EM radiation intersects the first plane of EM radiation at a line. An instrument is then moved toward the target along the line.

In another form, the present invention is carried out by a surgical guidance system for establishing a trajectory to a target located in a patient. The system includes a fixation frame. A first arc member coupled is to the fixation frame and has a radius. A second arc member is coupled to the fixation frame and has substantially the same radius as the first arc member. The first and second arc members are adjustably coupled to each other to rotate about a common axis. The system further includes first and second electromagnetic (EM) radiative sources coupled to the first and second arc members and configured to project first and second electromagnetic (EM) radiative beams which are viewable and which intersect to define the trajectory.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

Figure 1:
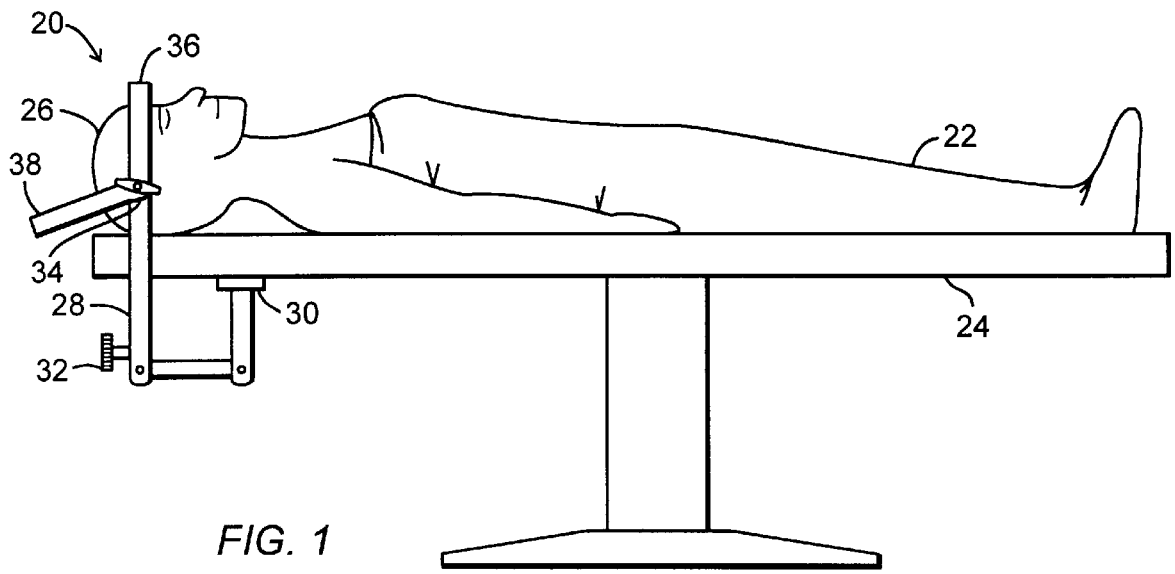
FIG. 1 shows a surgical guidance system and a patient each of which are coupled to a surgical table.

FIG. 1 shows a surgical guidance system 20 and a patient 22 each of which are coupled to a surgical table 24. Patient 22 is being prepared for surgery and may be anesthetized. Additionally, patient 22 is coupled to surgical table 24 using a conventional fixation device, such as a Mayfield headrest which is a three point fixation device that holds a skull in a fixed position during the surgery. FIG. 1 illustrates surgical guidance system 20 as being positioned around the head 26 of patient 22 because system 20 is particularly suited to endoscopic surgery within the brain. However, system 20 is not limited to brain or endoscopic surgeries. System 20 may be used in any surgery that involves directing a surgical instrument along a selected trajectory. System 20 may be manufactured from a sturdy, non-corrosive material such as stainless steel, in order for system 20 to withstand rigorous treatment and repeated sterilization.

Surgical guidance system 20 includes a fixation frame 28. Fixation frame 28 is an adjustment system that has a first end 30 secured to surgical table 24 relative to patient 22. A position adjustor 32 desirably having six degree-of-freedom position control couples to first end 30 through various mechanical linkages. A second end 34 is coupled to a first arc member 36 and a second arc member 38. Second end 34 couples through various mechanical linkages to position adjustor 32. Position adjustor 32 allows three dimensional movement of system 20 in two directions along x, y, and z axes so that system 20 can be positioned and secured relative to a target (discussed below) located inside head 26.

Figure 2:
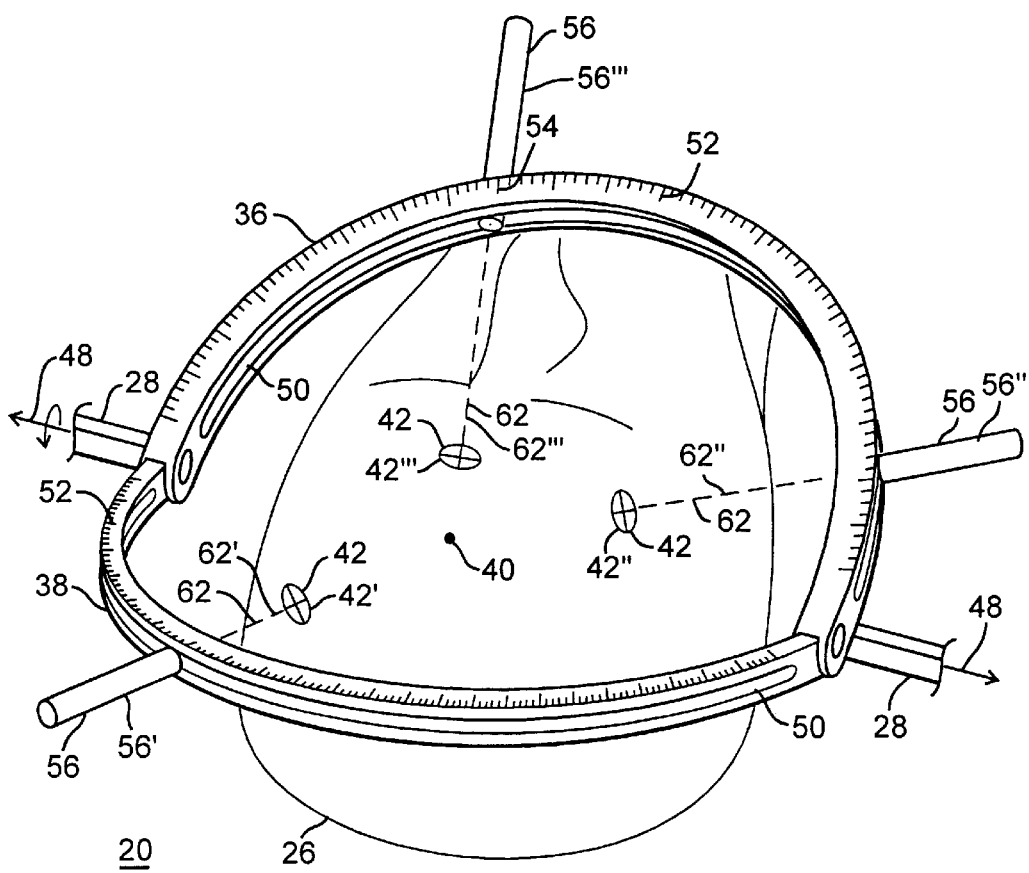
FIG. 2 shows a perspective view of first and second arc members of the surgical guidance system.

FIG. 2 shows a perspective view of first and second arc members 36 and 38, respectively, of surgical guidance system 20. First arc member 36 and second arc member 38 are positioned around head 26 relative to a target 40. Target 40 is located internal to head 26 and represents the surgical area of interest inside the brain. Fixed markers 42 are attached to head 26.

Conventionally, fixed markers 42 are placed on the patient's head by medical personnel prior to CT scans, MRI scans, or PET scans at locations where they will best be viewed on the scanned images relative to the region of interest in the brain. Those skilled in the art will recognize that imaging techniques are not limited to CT scans, MRI scans, or PET scans but may be some other type of imaging process that can accurately characterize landmarks in the brain. Images produced by any such imaging techniques will generally be referred to as scanned images in the following discussion.

Fixed markers 42 are made of a material that is visible on the scanned images of head 26 and are utilized as a reference to define a location of target 40. At least three fixed markers 42 are used to define the location of target 40 in a three dimensional volume, however, more than three fixed markers 42 may be placed on the patient's head in order to ensure that enough markers will be visible on the scanned images. In response to the scanned images, addresses are derived based on a three dimensional coordinate system for fixed markers 42 and target 40. Fixed markers 42 then remain attached to the patient's head and are used to align system 20 relative to target 40.

First and second arc members 36 and 38, respectively, are coupled to fixation frame 28, and each have substantially the same radius. First and second arc members 36 and 38 are adjustably coupled to each other to rotate about a common axis 48 to describe a virtual sphere of which common axis 48 is a diameter. Those skilled in the art will recognize that the virtual sphere is imaginary and that first and second arc members 36 and 38, respectively lie on the surface of the sphere. A central opening 50 is located on a centerline along an arc length of each of first and second arc members 36 and 38. In addition, position indication marks 52 are scribed onto first and second arc members 36 and 38. Marks 52 indicate an angular position along the arc length of either of first and second arc members 36 and 38 relative to an origin position 54.

Central opening 50 and marks 52 allow laser pointers 56 to be attached in positions that are moved in response to the target and marker addresses. Laser pointers 56 are point electromagnetic (EM) radiative sources that project laser beams 62. The mounting technique produces point electromagnetic (EM) radiative beams that are laser beams 62 oriented substantially perpendicular to a tangent of first and second arc members 36 and 38. Additionally, by mounting laser pointers 56 along central opening 50, laser beams 62 project through the centerline along the arc length of first and second arc members 36 and 38. Thus, laser beams 62 mounted anywhere along first arc member 36 or second arc member 38 project through a center point of the virtual sphere.

When system 20 is aligned so that target 40 is located at the center point of the virtual sphere, the trajectory of each of laser beams 62 is through target 40. When positioned in response to the locations of fixed markers 42 and target 40, laser beams 62 provide visual guidance for alignment of system 20 around head 26 relative to target 40. Laser pointers are used in the preferred embodiment because of the visible and coherent point source character of the laser beam. However, those skilled in the art will recognize that other electromagnetic radiative sources may be used that produce a coherent point that can be visually seen or electronically detected.

Figure 3:
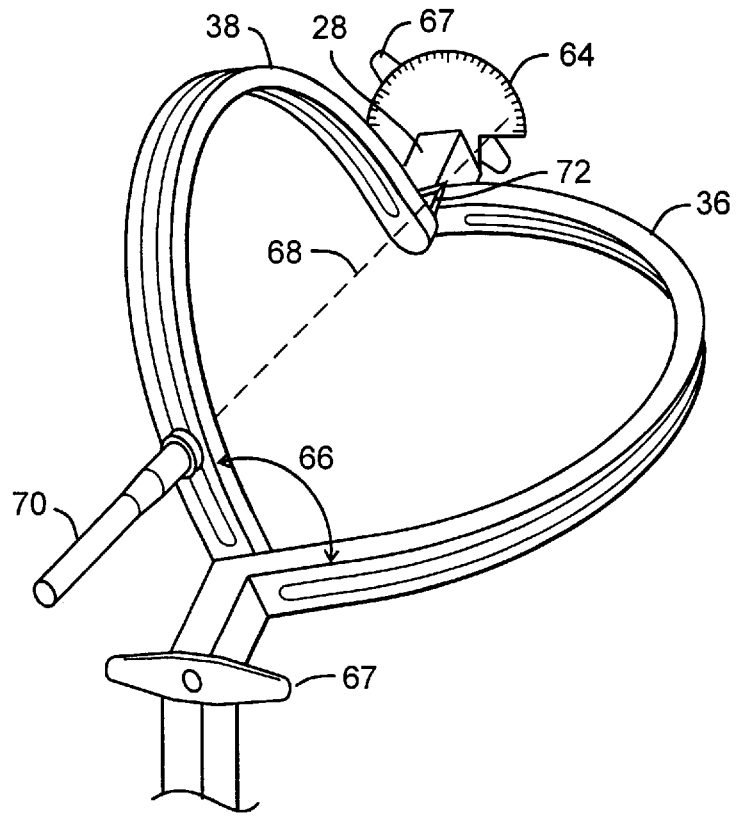
FIG. 3 shows a perspective view of a fold angle indicator mounted on a fixation frame for adjusting a fold angle between the first and second arc members.

FIG. 3 shows a perspective view of a fold angle indicator 64 mounted on fixation frame 28 for adjusting a fold angle 66 between first arc member 36 and second arc member 38. As discussed previously, first arc member 36 and second arc member 38 are adjustably coupled to rotate about common axis 48 (FIG. 2). The resulting angle between first arc member 36 and second arc member 38 is fold angle 66. Fold angle 66 is maintained by tightening knobs 67 to secure first and second arc members 36 and 38, respectively relative to each other.

Since fixed markers 42 (FIG. 2) are located in a three dimensional volume, it may be desired to adjust first arc member 36 and second arc member 38 relative to each other. Prior to surgery, a value for fold angle 66 is calculated in response to the marker addresses for fixed markers 42 and the target address for target 40. Fold angle 66 is then manually adjusted until a laser beam 68 being projected from a laser source 70 shines through an aperture 72 onto fold angle indicator 68 at an angular reading that identifies the calculated value for fold angle 66.

The strategy employed for aligning system 20 is to position system 20 so that each of three laser beams 62 (FIG. 2) intersects respective ones of fixed markers 42 along trajectories through the center point of the virtual sphere. When system 20 is spatially adjusted to cause three laser beams 62 to shine substantially concurrently on respective ones of fixed markers 42, position adjuster 32 (FIG. 1) is secured so that system 20 is fixed relative to target 40. This technique can be performed quickly and efficiently by medical personnel employing the immediate visual feedback of laser beams 62 on head 26. Thus, the amount of time requiring the involvement of the anesthetized patient is decreased. Additionally, this technique requires less extensive training than what is required to operate software programs and interpret data on computer displays.

Figure 4:
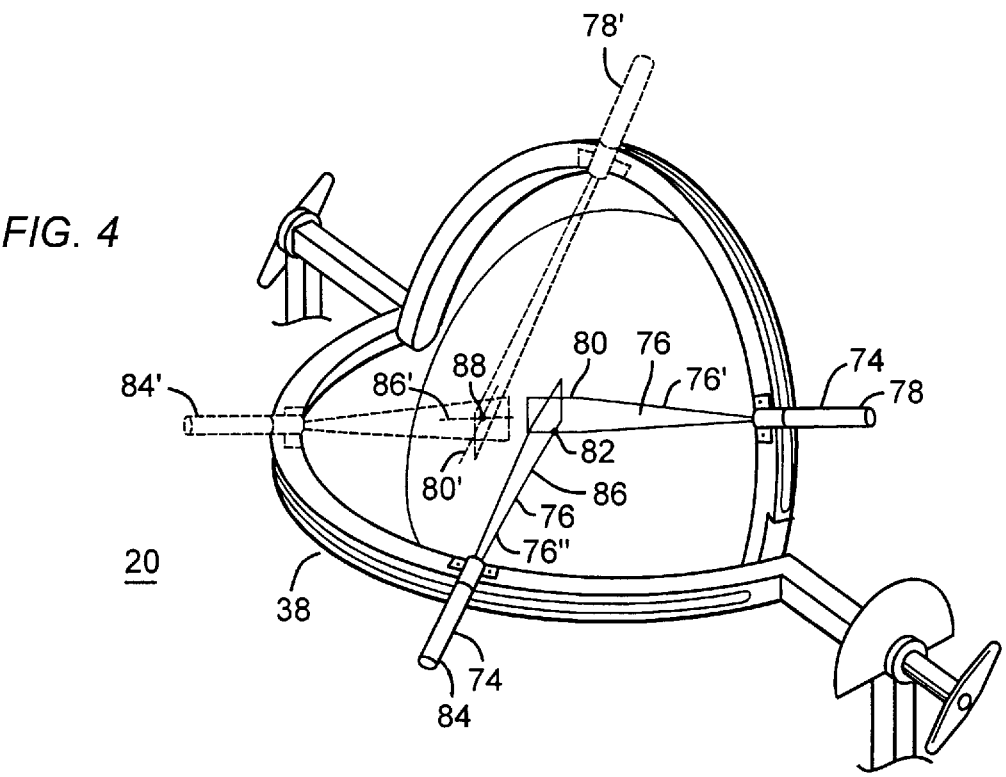
FIG. 4 shows a perspective view of the surgical guidance system configured with planar light sources that are projecting planar light beams.

FIG. 4 shows a perspective view of surgical guidance system 20 configured with planar light sources 74 that are projecting planar light beams 76. Once system 20 is aligned relative to target 40, a first planar light source 78 is attached anywhere along first arc member 36 or second arc member 38 so that a first plane of light 80 produced from a first planar light beam 76' intersects an initial surgical entry point 82. Initial surgical entry point 82 is selected by a surgeon prior to the surgery in response to the target address of target 40 and based on his or her knowledge of critical or eloquent areas of the brain. Additionally, a second planar light source 84 is attached anywhere along first arc member 36 or second arc member 38 so that a second plane of light 86 produced from a second planar light beam 76" intersects first plane of light 80 at initial surgical entry point 82. Second plane of light 86 desirably intersects first plane of light 80 in a roughly perpendicular manner to minimize ambiguity of the intersection point.

First planar light source 78 and second planar light source 84 are oriented so that planar light beams 76 project in planes that are substantially perpendicular to the planes in which first and second arc members 36 and 38, respectively, lie. Additionally, planar light beams 76 are substantially coincident with the radius of the virtual sphere described by first and second arc members 36 and 38, respectively. In the preferred embodiment, first and second planar light sources 78 and 84, respectively, are laser sources coupled with planar lens systems to shape the laser beams into planar laser beams. Those skilled in the art will recognize that other electromagnetic (EM) radiative source systems may be adapted to produce a similar effect. For example, a magnetic field generator or an radio frequency generator may be used for emitting the electromagnetic (EM) radiative beams to produce the desired planes of electromagnetic (EM) radiation.

The intersection of first plane of light 80 and second plane of light 86 forms a line. Due to the orientation of first planar light source 78 and second planar light source 84, the line indicates a trajectory to target 40 and would pass through target 40 but for being obstructed by head 26. First plane of light 80 and second plane of light 86 are continuously presented. Therefore, when an instrument is placed on the line and oriented substantially parallel to planar light beams 76, line segments corresponding to first and second planes of light 80 and 86, respectively shine on the shaft of the instrument. A surgical instrument is then propelled along the trajectory indicated by the line, through a burr hole made by the surgeon at initial surgical entry point 82 on head 26. The surgical instrument may be an optic instrument such as an endoscope, however, those skilled in the art will recognize that the instrument can be any conventional instrument used in such surgeries configured with a sensing system for detecting the line segments.

The strategy of propelling an instrument along a line in response to concurrently viewed segments of planes of light 80 and 86, provides immediate visual feedback to the surgeon which can shorten the surgery time since no time is spent interpreting data viewed on a computer screen.

Occasionally, the surgeon may select a second surgical entry point 88. This decision may be made by the surgeon, if he or she determines that the instrument will pass through a critical or eloquent area of the brain. Since target 40 is located at the center point of the virtual sphere described by first arc member 36 and second arc member 38, planar light sources 74 can be moved anywhere on first arc member 36 or second arc member 38, and the line formed by the intersection of planar light beams 76 will again establish a trajectory to target 40. For the same reason, fold angle 66 can be adjusted to any position practical to perform the surgery. Therefore, the surgeon can adjust planar light sources 74.

A first planar light source 78' and a second planar light source 84' indicate planar light sources 74 being moved to locate a new trajectory at second surgical entry point 88. First planar light source 78' is moved along arc member 36 and second planar light source 84' is moved along arc member 38 so that a first plane of light 80' and a second plane of light 86' intersect at second surgical entry point 88. The surgical instrument is then propelled along the new trajectory formed by the intersection of first plane of light 80' and second plane of light 86'.

Figure 5:
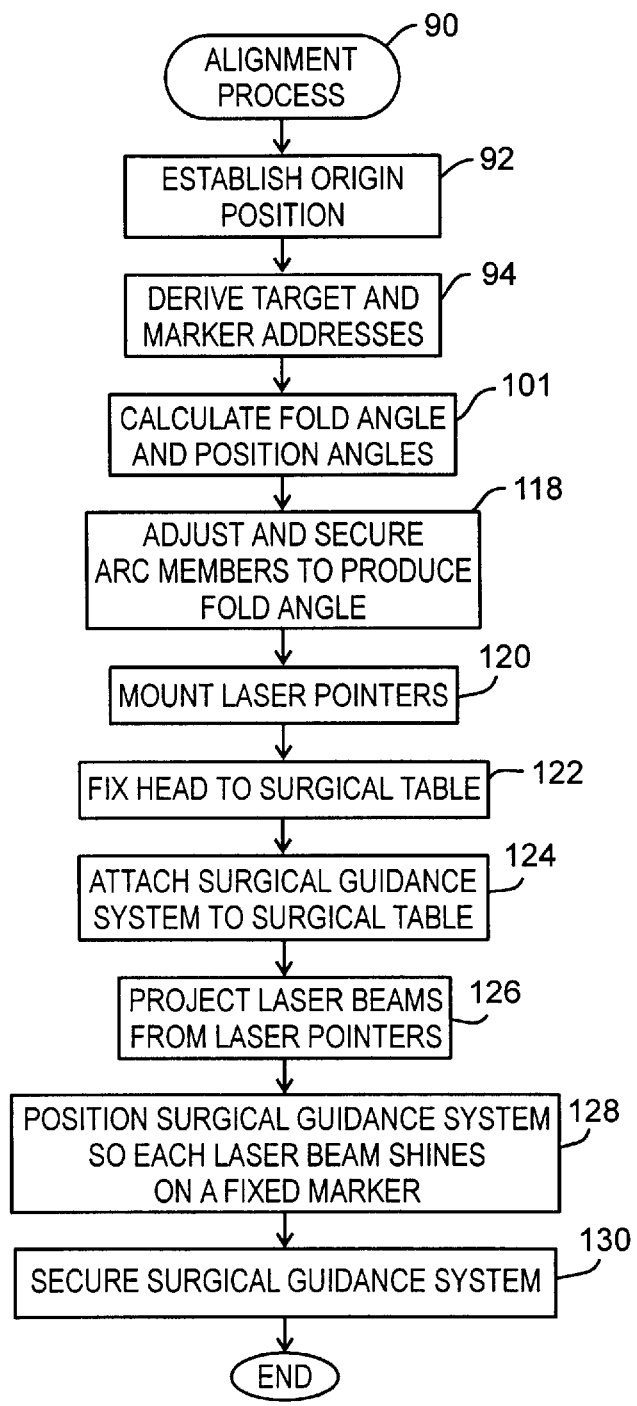
FIG. 5 is a flow diagram of an alignment process performed prior to surgery.
Figure 6:
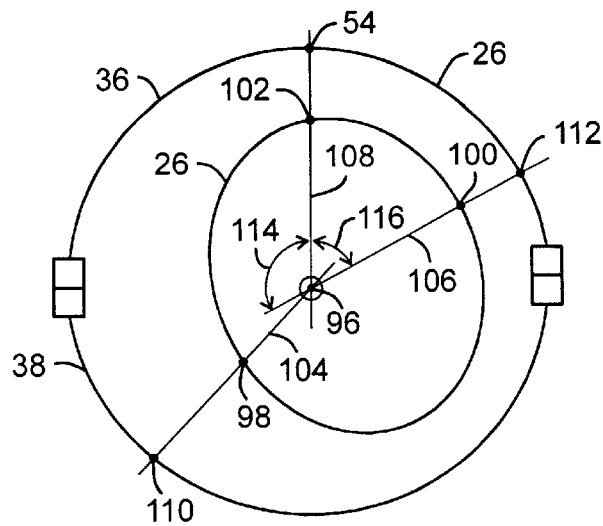
FIG. 6 is a schematic representation of virtual lines formed between a target and each of three marker addresses.

FIG. 5 is a flow diagram of an alignment process 90 performed prior to surgery. FIG. 6 is a schematic representation of virtual lines formed between a target address 96 and each of three marker addresses 98, 100, and 102 and is referred to while describing process 90. FIG. 6 illustrates the imaginary, or virtual, lines formed between pairs of points through an image of head 26 and how those virtual lines can be extended to identify positions along first and second arc members 36 and 38, respectively, for placing laser pointers 56.

Process 90 begins with a task 92 which establishes origin position 54 (FIG. 2) on system 20 from which subsequent calculations will be based. Origin position 54 is an arbitrary position and may be desirably centered between left and right sides of head 26 (FIG. 2)

In response to task 92, a task 94 is performed. Task 94 derives a target address 96 for target 40 (FIG. 2). Additionally, task 94 derives a first marker address 98 for a first fixed marker 42' (FIG. 2), a second marker address 100 for a second fixed marker 42" (FIG. 2), and a third marker address 102 for a third fixed marker 42'''. The target and marker addresses are obtained from the results of scanned images of head 26 and are based on a three dimensional coordinate system. The target and marker addresses are derived prior to surgery by entering scan data into a conventional microprocessor based computer system configured for medical, personal, or industrial use. Software programs resident in computer memory provide the necessary computational capability to derive addresses based on a three dimensional coordinate system using trigonometric techniques known to those skilled in the art.

Once the addresses are derived, a task 101 causes a computer program to calculate fold angle 66 (FIG. 3) and position angles along first and second arc members 36 and 38, respectively from the derived addresses. A first virtual line 104 (FIG. 6) is formed between target address 96 and first marker address 98. A second virtual line 106 (FIG. 6) is formed between target address 96 and second marker address 100. A third virtual line 108 is formed between target address 96 and third marker address 102. Those skilled in the art will recognize that first, second, and third virtual lines 104, 106, and 108, respectively, may be formed by the computer program in graphical or numerical form. Additionally, each of virtual lines 104, 106, and 108 are extended out from target address 96 through respective ones of marker addresses 98, 100, and 102 until intersecting with first arc member 36 or second arc member 38.

Products from task 101 include a first position 110, a second position 112, and fold angle 66 (FIG. 3). First position 110 is determined to be on one of first and second arc: members 36 and 38, respectively, along first virtual line 104. First position 110 is defined by fold angle 66 and a first position angle 114 relative to origin position 54. Likewise, second position 112 is determined to be on one of first and second arc members 36 and 38, respectively, along second virtual line 106. Second position 112 is defined by fold angle 66 and a second position angle 116 relative to origin position 54.

Following task 101, a task 118 adjusts and secures first arc member 36 and second arc member 38 to produce fold angle 66. Fold angle 66 is adjusted by medical personnel to the appropriate position by viewing laser beam 68 (FIG. 3) on fold angle indicator 64 (FIG. 3). Fold angle 66 is then maintained by tightening knobs 67 (FIG. 3) to secure first and second arc members 36 and 38, respectively.

After fold angle 66 is produced in task 118, a task 120 mounts laser pointers 56. A first laser pointer 56' (FIG. 2) is mounted by medical personnel at first position 110 by reading position indication marks 52 (FIG. 2) corresponding to first position angle 114. Likewise, a second laser pointer 56''' (FIG. 2) is mounted by medical personnel at second position 112 by reading position indication marks 52 corresponding to second position angle 116. A third laser pointer 56''' (FIG. 2) is then mounted by medical personal at origin position 54 (FIG. 2).

Following task 120, a task 122 fixes patient 22 (FIG. 1) to surgical table 24 (FIG. 1). Task 122 and subsequent tasks require the direct and continuous involvement of patient 22. Patient 22 may already be anesthetized, but the surgical site need not be prepped for the upcoming surgery. However, first, second, and third fixed markers 42', 42'', and 42''', respectively, are still attached to head 26. During task 122, head 26 (FIG. 1) is fixed using conventional and appropriate means such as a Mayfield headrest, so that head 26 is restricted from moving for the duration of the surgery.

Following task 122, a task 124 attaches system 20 (FIG. 1) to surgical table 24 (FIG. 1). During task 124, system 20 is secured at first end 30 (FIG. 1) relative to patient 22.

Following task 124, a task 126 projects laser beams 62 (FIG. 2) from laser pointers 56. During task 126, first laser pointer 56' is activated to project a first laser beam 62' (FIG. 2), second laser pointer 56'' is activated to project a second laser beam 62'' (FIG. 2), and third laser pointer 56''' is activated to project a third laser beam 62''' (FIG. 2).

In response to task 126, a task 128 aligns surgical guidance system 20 (FIG. 1). During task 128, medical personnel use position adjustor 32 (FIG. 1) to adjust system 20 along the x, y, and z axes relative to patient 22. System 20 is positioned so that first laser beam 62' (FIG. 2) from first laser pointer 56' (FIG. 2) shines on first fixed marker 42' (FIG. 2), second laser beam 62'' from second laser pointer 56'' shines on second fixed marker 42'', and third laser beam 62''' from third laser pointer 56''' shines on third fixed marker 42'''. When laser beams 62 shine on respective ones of fixed markers 42 substantially concurrently, system 20 is appropriately aligned.

Following task 128, a task 130 secures system 20 by immobilizing position adjustor 32. At this point, target 40 is located at the center point of a virtual sphere described by first arc member 36 and second arc member 38. Hereafter, the position of head 26 and the position of system 20 desirably remain fixed with respect to each other.

After task 130, process 90 is complete. At this point, head 26 may be prepared for surgery by clipping hair, cleaning the surgical site, marking initial surgical entry point 82 (FIG. 4), and so forth. To accommodate surgical preparation, system 20 may be disengaged from surgical table 24 (FIG. 1) at first end 30 (FIG. 1), sterilized, and reattached to surgical table 24 in substantially the same position relative to head 26 that system 20 was in prior to removal.

Figure 7:
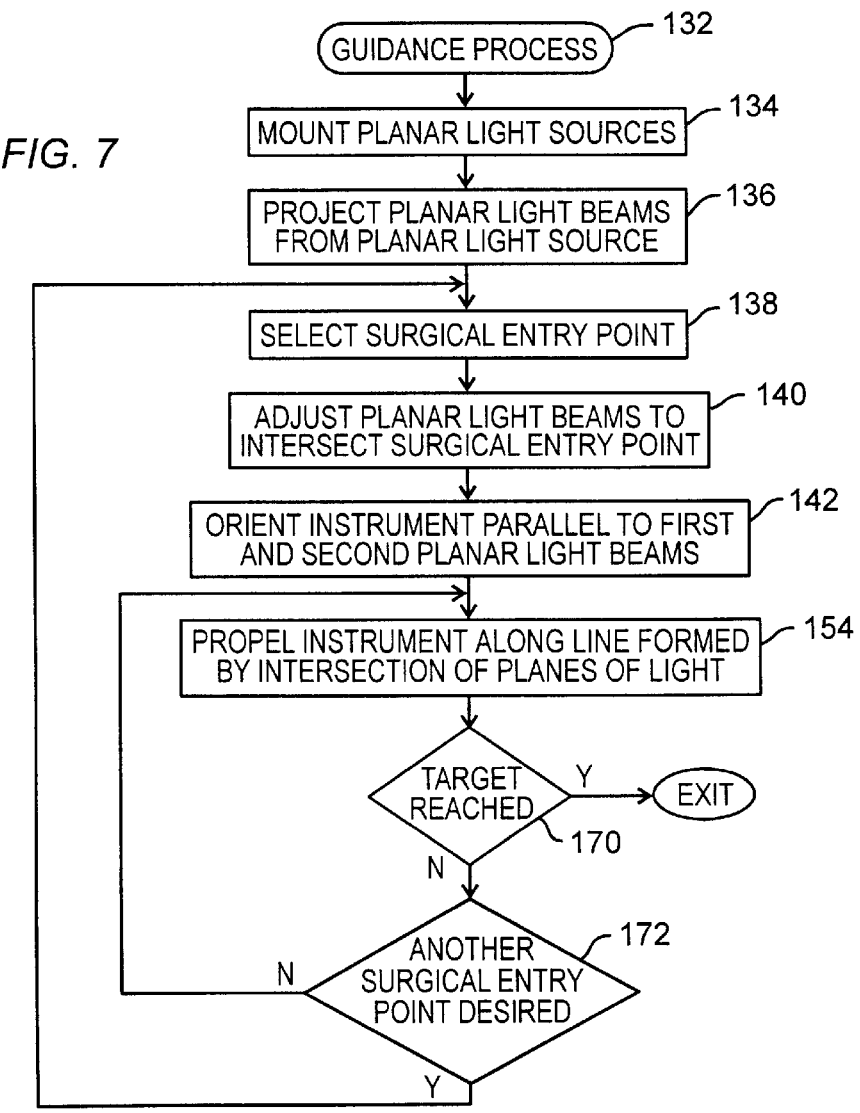
FIG. 7 is a flow diagram of a guidance process performed during surgery.

FIG. 7 is a flow diagram of a guidance process 132 performed during surgery. Process 132 is performed by the surgeon or assigned medical personnel using system 20 following alignment process 90 (FIG. 5) and after patient 22 (FIG. 1) is prepared for the surgery. Process 132, in conjunction with process 90, causes system 20 to establish a trajectory to target 40 (FIG. 2).

Process 132 begins with a task 134. During task 134, first planar light source 78 (FIG. 4) and second planar light source 84 (FIG. 4) are mounted on either of first arc member 36 (FIG. 1) or second arc member 38 (FIG. 1) as desired. To maintain a sterile operating field, first planar light source 78 and second planar light source 84 are desirably sterilized prior to mounting.

Following task 134, a task 136 continuously projects planar light beams 76 (FIG. 4) from planar light sources 74 (FIG. 4). During task 136, first planar light source 78 is activated to produce first plane of light 80 (FIG. 4). Likewise, second planar light source 84 is activated to produce second plane of light 86 (FIG. 4).

Following task 136, a task 138 selects a surgical entry point. It will be readily apparent to those skilled in the art that initial surgical entry point 82 (FIG. 4) will have been selected prior to task 138. A surgeon may select initial surgical entry point 82 in response to the scanned images received prior to any surgery. Task 138 serves to confirm the location of initial surgical entry point 82.

In response to task 138, a task 140 adjusts first planar light beam 76' (FIG. 4) and second planar light beam 76'' (FIG. 4) to intersect initial surgical entry point 82. During task 140, first planar light source 78 is adjusted so that first plane of light 80 intersects initial surgical entry point 82. Likewise, second planar light source 84 is adjusted so that second plane of light 86 intersects first plane of light 80 at initial surgical entry point 82.

Figure 8:
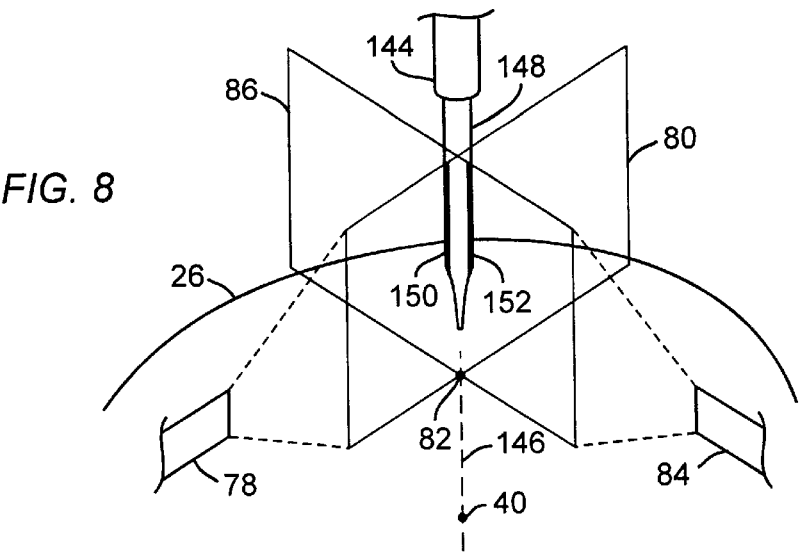
FIG. 8 is a schematic representation of an instrument directed along a trajectory formed by the intersection of planar light beams.

Following adjustment task 140, a task 142 causes a surgical instrument to be oriented parallel to first and second planes of light 80 and 86, respectively. FIG. 8 is a schematic representation of an instrument 144 directed along a trajectory 146 formed by the intersection of first plane of light 80 and second plane of light 86.

First and second planar light sources 78 and 84, respectively, are adjusted so that first and second planes of light 80 and 86, respectively, intersect at initial surgical entry point 82 on head 26 (FIG. 1). Instrument 144 is oriented substantially parallel to first plane of light 80 so that a first line segment 150 of first plane of light 80 is viewed along a shaft 148 of instrument 144. Likewise, instrument 144 is oriented substantially parallel to second plane of light 86 so that a second line segment 152 of second plane of light 86 is viewed along shaft 148. Instrument 144 is appropriately aligned along trajectory 146 when first line segment 150 and second line segment 152 are concurrently viewed along shaft 148.

Following orientation task 142, a task 154 (FIG. 7) is performed. Task 154 causes instrument 144 (FIG. 8) to be propelled along the line formed by the intersection of first plane of light 80 and second plane of light 86. The surgeon propels instrument 144 along trajectory 146 (FIG. 8), formed by the continuously presented line, toward target 40 by viewing first line segment 150 (FIG. 8) and second line segment 152 (FIG. 8) concurrently on shaft 148 (FIG. 8).

Figure 9:
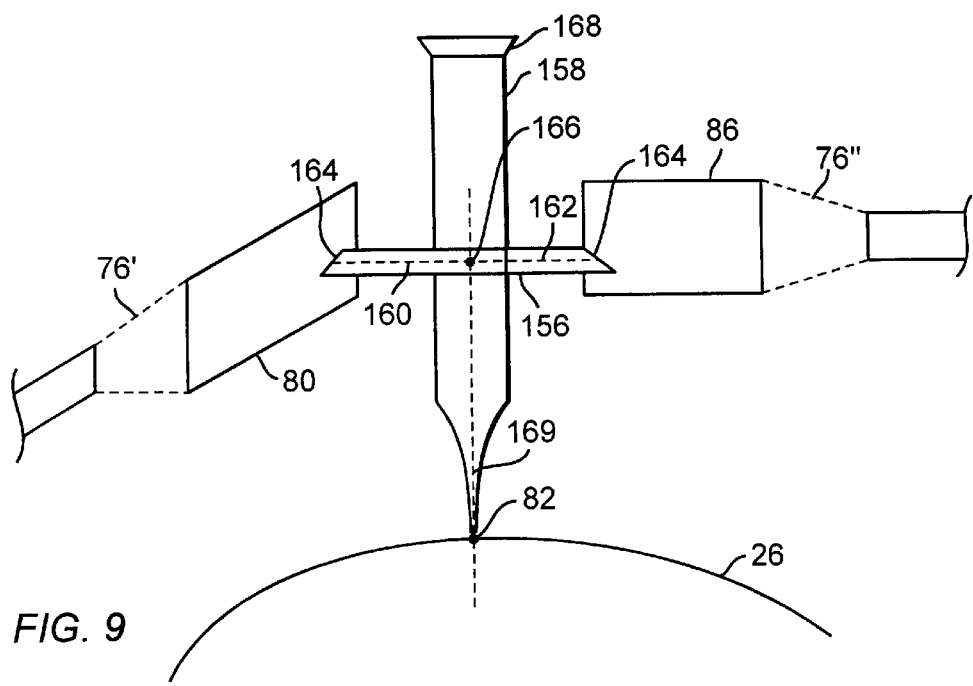
FIG. 9 is a schematic representation of a line generator mounted on an optic instrument.

In an alternate embodiment, the surgeon may view a representation of the intersection of first plane of light 80 and second plane of light 86 through an optic instrument, such as a surgical microscope to perform tasks 142 and 154. FIG. 9 is a schematic representation of a line generator 156 mounted on an optic instrument 158 that has a viewing port 168. Line generator 156 is manufactured from a transparent material, such as glass, and has a beveled edge 164. Line generator 156 is substantially planar, and the orientation of line planar surface of line generator 156 is perpendicular to the viewing axis of optic instrument 158.

A first light 160 is refracted at beveled edge 164 and projected through line generator 156 in response to first planar light beam 76'. Likewise, a second light 162 is refracted at beveled edge 164 and projected through line generator 156 in response to second planar light beam 76". First light 160 and second light 162 intersect at a center point 166 of line generator 156. Center point 166 indicates a trajectory to target 40 located in head 26.

Figure 10:
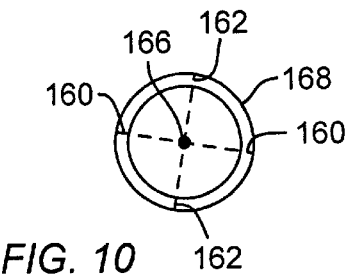
FIG. 10 is a view of a first light and a second light through a viewing port of the optic instrument.

FIG. 10 is a view of first light 160 and second light 162 through viewing port 168 of optic instrument 168. First light 160 and second light 162 need not intersect, but may be viewable as hashmarks on a frame seen through viewing port 168. Since initial surgical entry point 82 (FIG. 4) and the planar surface of line generator 156 is spaced a distance apart, the line defined by center point 166 and initial surgical entry point 82 forms a trajectory for optic instrument 158. The surgeon then looks through viewing port 168 and manipulates optic instrument 158 along the trajectory by viewing first light 160 and second light 162 through viewing port 168.

In the preferred embodiment, light is projected through a line generator for immediate viewing of hashmarks that indicate a trajectory. However, those skilled in the art will recognize that other electromagnetic (EM) emissions can be projected through the line generator. The line generator can then be configured to convert the EM emissions into a form that is quickly and easily detectable by the surgeon.

In response to task 154 (FIG. 7), a query task 170 determines if target 40 is reached. The present invention complements conventional depth detection techniques which include but are not limited to physically mounting depth indicators on the instrument. When target 40 is reached procedure 132 is exited and the surgeon carries on with the surgery. This may include placing a shunt, removing a tumor, excising tissue for biopsy, and so forth.

In query task 170, when target 40 is not reached, process 132 proceeds to a query task 172. Query task 172 determines if another surgical entry point is desired. The surgeon may decide to select second surgical entry point 88 (FIG. 4) if he or she determines that by proceeding along the current trajectory, a critical area of the brain may be damaged. For example, the surgeon may determine that he or she will damage a blood vessel located along the trajectory, that could cause excessive bleeding. If another surgical entry point is not desired, process 132 loops back to task 154, and the surgeon continues to propel instrument 144 toward target 40.

When a surgeon determines that another surgical entry point is desired in query task 172, process 132 loops back to task 138 so that second surgical entry point 88 can be selected and a trajectory can be formed along which instrument 144 may be propelled. As discussed above, a new trajectory is formed by adjusting fold angle 66 and positioning planar light sources 74 as desired, to indicate the new trajectory through second surgical entry point 88.

In an alternate embodiment, electromagnets may be employed as the electromagnetic (EM) radiative sources in place of planar light sources 74 described in connection with surgical guidance system 20 (FIG. 4). In this alternate embodiment, a magnetic field generator includes at least a first electromagnet and a second electromagnet. The first and second electromagnets are formed from a wire coil wound around a cylindrical iron or steel core in a tight helix. A magnetic field is produced by the periodic generation of electromagnetic, (EM) radiative beams. The first and second electromagnets can be alternatively driven such that each of the EM radiative beams do not interfere with one another.

According to one aspect of the alternate embodiment, the magnetic field generated by the first electromagnet may define a first magnetic center located centrally along a longitudinal axis associated with the first electromagnet. Magnetic flux lines intersect the center line at substantially a right angle. Thus, in three dimensional space, a first plane of electromagnetic (EM) radiation that perpendicularly bisects the first electromagnet through the magnetic center is defined by the orientation of the magnetic field.

Similarly, a second plane of electromagnetic (EM) radiation is generated by the second electromagnet. Referring to FIG. 4, the electromagnets may be mounted on first or second arc members 36 and 38, respectively, so that the center line for each of the electromagnets is substantially perpendicular to a tangent of first or second arc members 36 and 38 and substantially coincident with the radius of the virtual sphere defined by arc members 36 and 38, respectively. The first and second planes of electromagnetic (EM) radiation are then directed toward initial surgical entry point 82 such that the intersection of first and second planes of electromagnetic radiation intersect to form a line. Like surgical guidance system 20, the line defines a trajectory through the initial surgical entry point 82 to target 40 (FIG. 2).

Referring to FIG. 8, at least two magnetic field sensors (not shown) may be located on instrument 144. The magnetic field sensors are preferably aligned with shaft 148 of surgical instrument 144, and the system is configured so that the magnetic field is oriented perpendicular to trajectory 146. Those skilled in the art will recognize that the guidance system may be configured such that the electromagnets are located on instrument 144 and the magnetic field sensors are located along first and second arc members 36 and 38, respectively.

The orientation of the magnetic field is detected by the sensors and the sensors will simultaneously detect a null (zero magnitude) in the magnetic field when they both are substantially collinear with the magnetic center. In other words, the magnetic field sensors detect the null in the magnetic field anywhere along trajectory 146. This detected null is then converted into a form that can be visually interpreted by the surgeon. Those skilled in the art will recognize that this conversion and subsequent feedback of instrument movement along the trajectory may be performed using a processor and a computer display.

In summary, the present invention provides an improved surgical guidance method and system for directing an instrument to a target within a body. The system has a reduced level of complexity so that the expenses associated with purchase of the surgical guidance system and subsequent training is reduced. Furthermore, calibration and set-up time involving the anesthetized patient is reduced, and a surgeon can quickly and easily select a another surgical entry point and trajectory to a target as needed.

Although the preferred embodiments of the invention have been illustrated and described in detail, it will be readily apparent to those skilled in the art that various modifications may be made therein without departing from the spirit of the invention or from the scope of the appended claims. For example, surgical guidance system 20 may be used in conjunction with a system that provides feedback of the actual position of the tip of an instrument. Additionally, the electromagnetic (EM) radiative sources may be magnetic field generators, radio frequency generators, infrared (IR) beacons, and so forth.

What is claimed is:

1. A guidance method for directing an instrument to a target, said method comprising the steps of:
   (a) deriving a target address for said target;
   (b) deriving a marker address for each of a plurality of fixed markers;
   (c) aligning a guidance device in response to said target address and said marker addresses;
   (d) projecting a first electromagnetic (EM) radiative beam from said guidance device to produce a first plane of electromagnetic (EM) radiation;
   (e) projecting a second planar electromagnetic (EM) radiative beam from said guidance device to produce a second plane of electromagnetic (EM) radiation, said second plane of EM radiation intersecting said first plane of EM radiation at a line; and
   (f) moving said instrument toward said target along said line.

2. A method as claimed in claim 1 wherein said guidance device comprises first and second point electromagnetic (EM) radiative sources, and said step (c) comprises the steps of:
   establishing an origin position on said guidance device;
   calculating first and second positions on said guidance device relative to said origin position, each of said first and second positions being responsive to said target address and one of said marker addresses; and
   mounting said first and second point EM radiative sources substantially at each of said first and second positions respectively, said first and second point EM radiative sources being respectively mounted to produce first and second point electromagnetic (EM) beams substantially perpendicular to a tangent of said guidance device.

3. A method as claimed in claim 2 wherein said guidance device comprises a first arc member having a radius and a second arc member having substantially said radius, said first and second arc members being adjustably coupled to rotate about a common axis, and said calculating step comprises the steps of:
   forming a first virtual line between said target address and a first one of said marker addresses;
   determining said first position on one of said first and second arc members along said first virtual line, said first position being defined by a fold angle between said first and second arc members about said common axis and a first position angle along said first and second arc members relative to said origin position;
   forming a second virtual line between said target address and a second one of said marker addresses; and
   determining said second position on one of said first and second arc members along said second virtual line, said second position being defined by said fold angle and a second position angle along said first and second arc members.

4. A method as claimed in claim 3 wherein said first and second positions are substantially on a centerline along an arc length of said first and second arc members.

5. A method as claimed in claim 3 wherein said step (c) further comprises the steps of:
   adjusting said first and second arc members about said common axis to produce said fold angle between said first and second arc members; and
   securing said first and second arc members to maintain said fold angle.

6. A method as claimed in claim 2 wherein said guidance device comprises a third point electromagnetic (EM) radiative source and said mounting step further comprises the step of mounting said third point EM radiative source at said origin position, said origin position being substantially on a centerline along an arc length of said first and second arc members.

7. A method as claimed in claim 6 wherein:
   said target is located inside a patient, said patient being in a fixed position;
   said guidance device is coupled to an adjustment system, said adjustment system being fixed relative to said patient;
   said first point EM radiative beam from said first point EM radiative source is directed toward a first one of said fixed markers;
   said second point EM radiative beam from said second point EM radiative source is directed toward a second one of said fixed markers;
   a third point electromagnetic (EM) radiative beam from said third point EM radiative source is directed toward a third one of said fixed markers; and
   said step (c) additionally comprises the step of positioning said guidance device to cause each of said first, second, and third point EM radiative beams to shine on said first, second, and third fixed markers respectively.

8. A method as claimed in claim 7 wherein said positioning step additionally comprises the step of securing said guidance device relative to said target.

9. A method as claimed in claim 1 wherein:

said target is located inside a patient, said patient being in a fixed position;

said method further comprises the step of selecting an initial surgical entry point on said patient;

said step (d) comprises the step of adjusting said first EM radiative beam so that said first plane of EM radiation intersects said initial surgical entry point; and said step (e) comprises the step of adjusting said second EM radiative beam so that said second plane of EM radiation intersects said first plane of EM radiation at said initial entry point.

10. A method as claimed in claim 9 additionally comprising, after steps (d) and (e), the steps of:

selecting a second surgical entry point on said patient;

adjusting said first EM radiative beam so that said first plane of EM radiation intersects said second surgical entry point; and adjusting said second EM radiative beam so that said second plane of EM radiation intersects said second entry point.

11. A method as claimed in claim 1 wherein said line forms a trajectory to said target and said step (f) further comprises the step of continuously presenting said line.

12. A method as claimed in claim 1 wherein said step (f) comprises the steps of:

orienting said instrument substantially parallel to said first plane of EM radiation to detect a first line segment of said first plane of EM radiation along a shaft of said instrument;

orienting said instrument substantially parallel to said second plane of EM radiation to detect a second line segment of said second plane of EM radiation along said shaft of said instrument, said first and second line segments being concurrently detected along said shaft; and propelling said instrument toward said target in response to concurrently detected first and second line segments.

13. A method as claimed in claim 1 wherein said instrument is an optic instrument, said instrument comprises a line generator, and said step (f) additionally comprises the steps of:

projecting a first electromagnetic (EM) emission through said line generator to be visible at a viewing port of said optic instrument, said first EM emission being projected in response to said first EM radiative beam;

projecting a second electromagnetic (EM) emission through said line generator to be visible at said viewing port of said optic instrument, said second EM emission being projected in response to said second EM radiative beam;

viewing said first and second EM emissions through said viewing port of said optic instrument; and manipulating said optic instrument so that said first and second EM emissions intersect to indicate a trajectory to said target.

14. A surgical guidance system establishing a trajectory to a target located in a patient, said system comprising:

a fixation frame;

a first arc member coupled to said fixation frame, said first arc member having a radius;

a second arc member coupled to said fixation frame, said second arc member having substantially said radius, and said first and second arc members being adjustably coupled to each other to rotate about a common axis; and first and second electromagnetic (EM) radiative sources coupled to said first and second arc members and configured to project first and second electromagnetic (EM) radiative beams which are detectable and which intersect to define said trajectory.

15. A system as claimed in claim 14 wherein said fixation frame comprises:

a first end secured relative to said patient;

a position adjustor coupled to said first end, said position adjustor having six degree-of-freedom position control; and a second end coupled to said first and second arc members and said position adjustor.

16. A system as claimed in claim 14 wherein said fixation frame comprises a fold angle indicator, said indicator being configured to identify a fold angle between said first and second arc members about said common axis.

17. A system as claimed in claim 14 wherein:

each of said first and second arc members have a central opening along an arc length of said arc member; and said system additionally comprises a plurality of laser pointers movably attachable to said first and second arc members, said laser pointers being configured to project a laser beam through said central opening to a center point of a virtual sphere described by said first and second arc members.

18. A system as claimed in claim 14 wherein:

each of said first and second EM radiative sources comprise a laser source movably attachable to one of said first and second arc members;

said first and second EM radiative beams are planar laser beams; and each of said laser sources is configured to project one of said planar laser beams.

19. A system as claimed in claim 14 wherein said EM radiative sources are oriented so that said first and second EM radiative beams project from said first and second arc members in a plane substantially perpendicular to said arc members and substantially coincident with said radius.

20. A surgical instrument guidance method for establishing a trajectory to a target located inside a patient, said method comprising the steps of:

(a) obtaining a target address for said target;

(b) obtaining a marker address for each of a plurality of markers fixed to said patient;

(c) providing a guidance device configured to be aligned relative to said target in response to each of said target and marker addresses;

(d) projecting a first planar light beam from said guidance device to produce a first plane of light; and (e) projecting a second planar light beam from said guidance device to produce a second plane of light, said second plane of light intersecting said first plane of light at a line which defines a trajectory to said target.

21. A method as claimed in claim 20 wherein said guidance device comprises first, second, and third point light sources, and said method additionally comprises, prior to said step (d), the steps of:

calculating first and second positions relative to an origin position on said guidance device, each of said first and second positions being responsive to said target address and one of said marker addresses, said first, second, and origin positions being supplied for mounting first, second, and third point light sources, respectively;

projecting a first point light beam from said first point light source toward a first one of said fixed markers;

projecting a second point light beam from said second point light source toward a second one of said fixed markers; and projecting said third point light beam from said third point light source toward a third one of said fixed markers;

wherein, said guidance device can be positioned to cause each of said first, second, and third light beams to shine on said first, second, and third fixed markers respectively.

22. A method as claimed in claim 20 wherein:

said provided guidance device comprises a six degree-of-freedom position controller adjusted in response to each of said received target and marker addresses; and said step (c) comprises the step of configuring said guidance device to be spatially adjusted and fixed relative to said target.

23. A method as claimed in claim 20 wherein:

said guidance device comprises a first arc member having a radius and a second arc member having substantially said radius, said first and second arc members being adjustably coupled to rotate about a common axis; and said method further comprises the step of continuously projecting said first and second planar light beams from one of said first and second arc members in a plane perpendicular to said arc member and coincident with said radius of said arc member.

* * * * *